United States Patent [19]
Asher et al.

[11] Patent Number: 5,113,685
[45] Date of Patent: May 19, 1992

[54] APPARATUS FOR CONTOURING SPINE PLATES AND/OR RODS

[75] Inventors: Marc A. Asher, Prairie Village, Kans.; Walter E. Strippgen, Golden, Colo.; Charles F. Heinig, Charlotte, N.C.; William L. Carson, Columbus, Mo.

[73] Assignee: AcroMed Corporation, Cleveland, Ohio

[21] Appl. No.: 646,835

[22] Filed: Jan. 28, 1991

[51] Int. Cl.⁵ .............................................. B21J 13/08
[52] U.S. Cl. ........................................ 72/458; 72/459; 140/106; 606/101
[58] Field of Search ............... 128/69; 606/61, 69, 606/101; 72/458, 459, 479; 140/106

[56] References Cited

U.S. PATENT DOCUMENTS

| | | | |
|---|---|---|---|
| 1,736,585 | 11/1929 | Fehlhaber | 72/458 X |
| 2,675,723 | 4/1954 | Stein | 72/458 |
| 2,678,573 | 5/1954 | Taylor | 72/458 |
| 2,723,578 | 11/1955 | Konola | 72/458 |
| 2,737,835 | 3/1956 | Herz | 606/101 |
| 3,179,129 | 4/1965 | Hahn | 140/106 |
| 4,034,595 | 7/1977 | Smith | 72/458 |
| 4,292,834 | 10/1981 | Tishler et al. | 72/458 X |
| 4,611,581 | 9/1986 | Stefee | |
| 4,648,388 | 3/1987 | Stefee | |
| 4,836,196 | 6/1989 | Park et al. | |
| 4,854,311 | 8/1989 | Steffee | |
| 4,887,595 | 12/1989 | Heinig et al. | 606/72 X |
| 4,955,886 | 9/1990 | Pawluk | 606/69 |

FOREIGN PATENT DOCUMENTS 8702572  5/1987  World Int. Prop. O. .......... 606/101

OTHER PUBLICATIONS

Journal of Bone & Joint Surgery; "Jewett Benders", p. 6; vol. 35-A, Jul. 1953.
1981 Zimmer Catalog entitled Optional Instruments for 2300-01 Basic Instrument Set, p. B114.
1981 Zimmer Catalog, p. B216.

*Primary Examiner*—Richard J. Apley
*Assistant Examiner*—Linda C. M. Dvorak
*Attorney, Agent, or Firm*—Tarolli, Sundheim & Covell

[57] ABSTRACT

A plurality of instruments or members are provided to plastically deform spine plates or rods to a configuration which corresponds to a desired configuration for connection with a spinal column. A pair of flat benders have slots which are engageable with a spine plate to bend and/or twist the spine plate. A pair of tube benders are engageable with a rod to bend the rod. One of the flat benders may be used with one of the tube benders to form a bend in the rod. In addition, the two flat benders may be used together to bend the rod. These instruments make possible two dimensional bending of spine plates and three dimensional bending of spine rods.

3 Claims, 6 Drawing Sheets

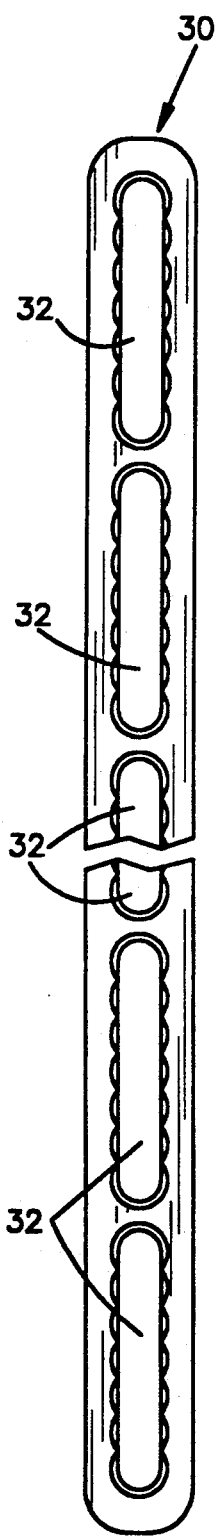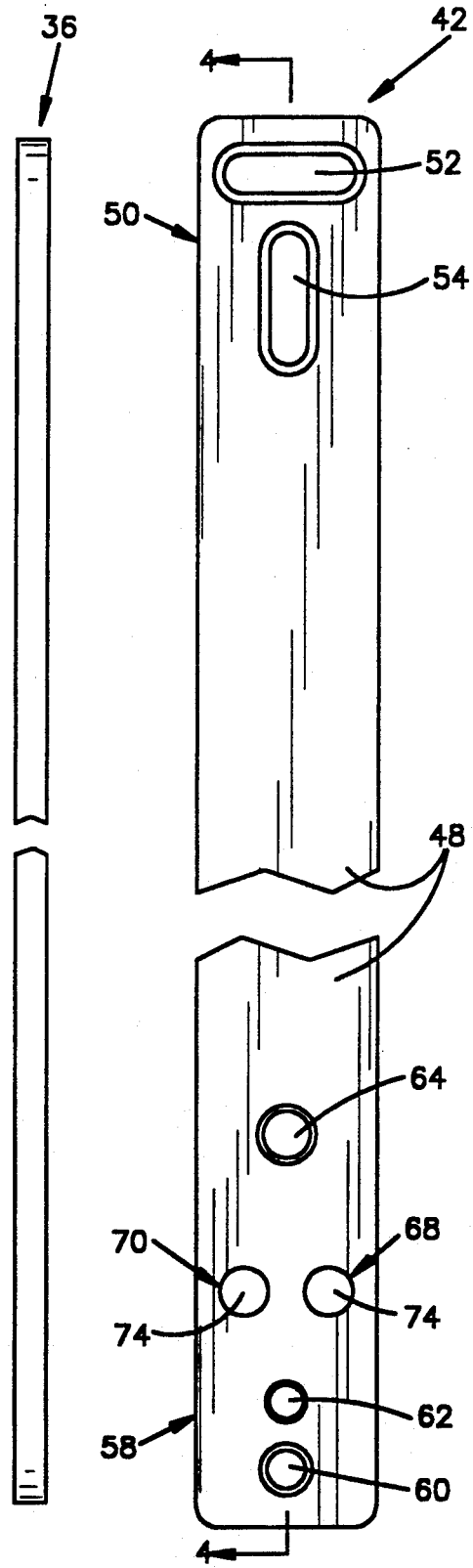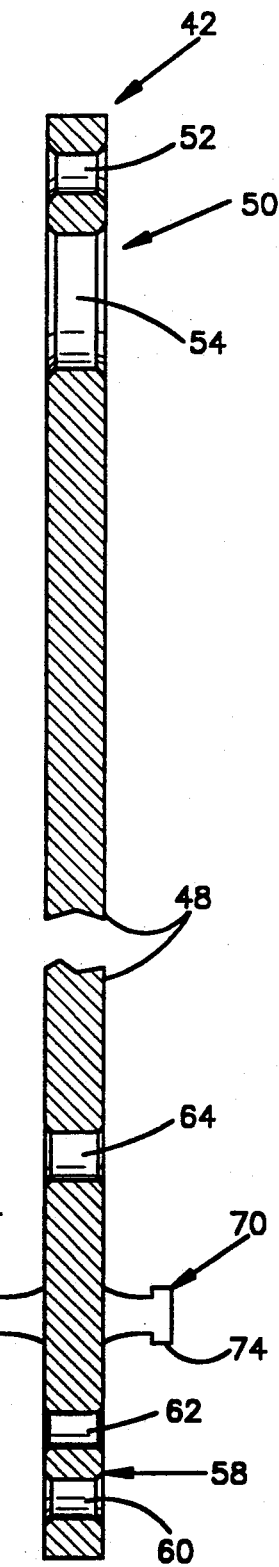
Fig.1　Fig.2　Fig.3　Fig.4

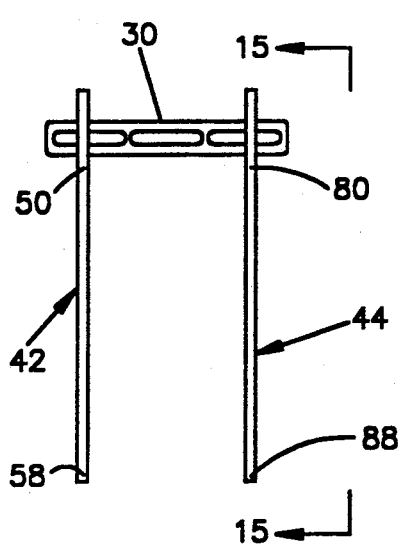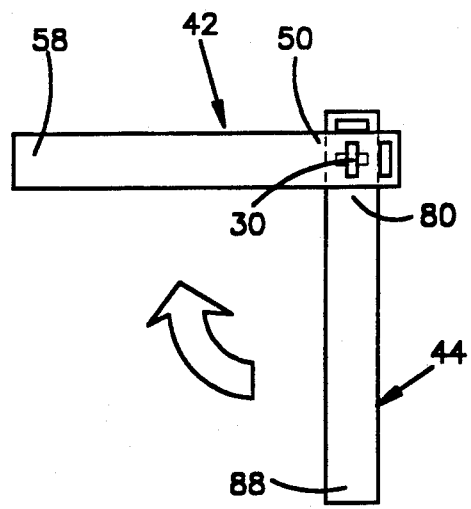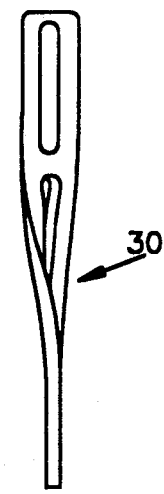
Fig.14   Fig.15   Fig.16
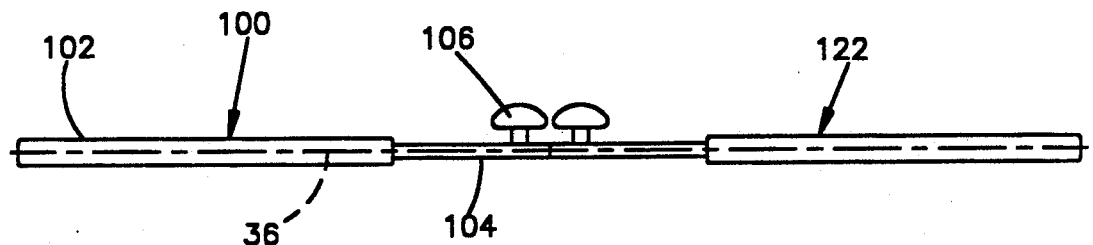
Fig.17
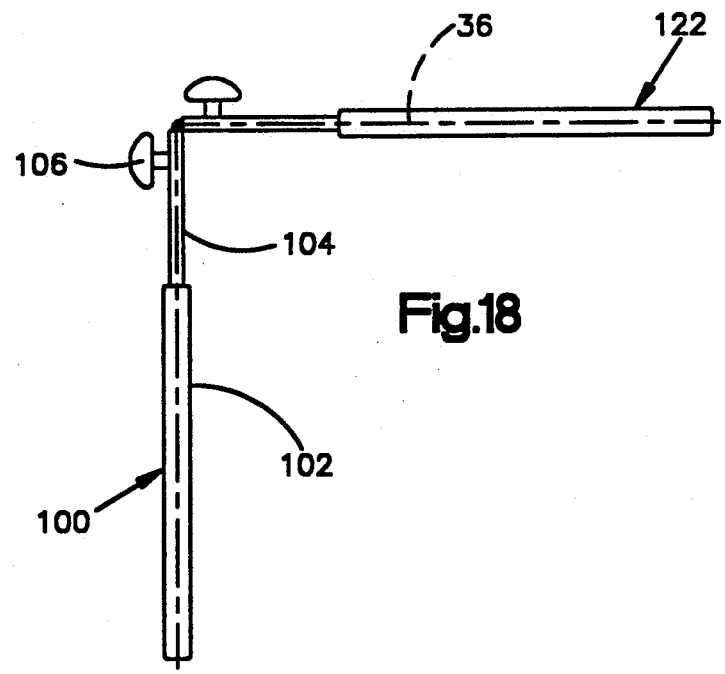
Fig.18

APPARATUS FOR CONTOURING SPINE PLATES AND/OR RODS

BACKGROUND OF THE INVENTION

The present invention relates generally to the corrections of spinal deformities. Specifically, the present invention relates to a method and apparatus for deforming spine plates and/or rods to a desired configuration for connection with a spinal column.

The human spine normally has contours in the sagittal plane. A deformed human spine has contours in other planes. For these reasons, it is a common need to contour plates or rods prior to placement in the spine. The use of rods or plates to position vertebra in a human spine is disclosed in U.S. Pat. Nos. 4,611,581; 4,648,388; 4,719,905; and 4,836,196.

Due to the differences in human spinal columns, particularly deformed spinal columns, during an operation it is desirable to be able to bend a spine plate or rod to the configuration of the spine to which it is to be connected. Thus, it is desirable to have a surgeon be able to view a spine to which a rod or plate is to be connected and then deform the rod or plate to a configuration which is a function of the configuration of the spine with which the rod or plate is to be connected.

SUMMARY OF THE INVENTION

The present invention provides a new and improved method and apparatus for use in plastically deforming spine plates and/or rods to a desired configuration for connection with a spinal column. The apparatus for plastically deforming the spine plates and/or rods includes a pair of flat benders which are engageable with either a spine plate or rod and a pair of tube benders which are engageable with a rod. The flat benders may be used to bend and/or twist a spine plate. The flat benders may also be used either together or with a tube bender to bend a rod.

BRIEF DESCRIPTION OF THE DRAWINGS

The foregoing and other features of the invention will become more apparent upon a consideration of the following description taken in connection with the accompanying drawings, wherein:

FIG. 1 is a plan view of a metal spine plate prior to deformation of the spine plate to a desired configuration for connection with a spinal column;

FIG. 2 is a plan view of a cylindrical metal rod prior to deformation of the rod to a desired configuration for connection with a spinal column;

FIG. 3 is a plan view of a flat bender which may be used to deform either the spine plate of FIG. 1 or the rod of FIG. 2;

FIG. 4 is a sectional view, taken generally along the line 4—4 of FIG. 3, further illustrating the construction of the flat bender;

FIG. 14 is a schematic illustration depicting the manner in which the flat benders of FIGS. 3 and 5 engage the spine plate of FIG. 1 prior to twisting of the spine plate;

FIG. 15 is a side elevational view, taken generally along the line 15—15 of FIG. 14, illustrating the relationship between the flat benders after twisting of the spine plate;

FIG. 16 is an illustration of the spine plate which has been twisted by using the flat benders in the manner illustrated schematically in FIGS. 14 and 15;

FIG. 17 is a schematic illustration depicting the manner in which a pair of tube benders of FIG. 7 engage a rod prior to bending of the rod;

FIG. 18 is a plan view illustrating the relationship between the tube benders of FIG. 17 after the rod has been bent with the pair of tube benders;

DESCRIPTION OF SPECIFIC PREFERRED EMBODIMENTS OF THE INVENTION

Implantable Members

Figure 5:
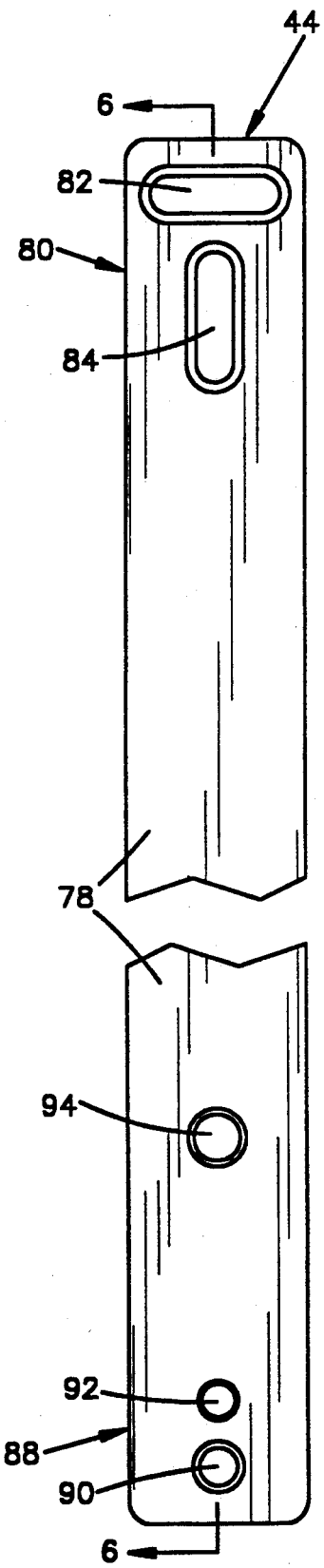
FIG. 5 is a plan view, generally similar to FIG. 4, of a second flat bender.
Figure 6:
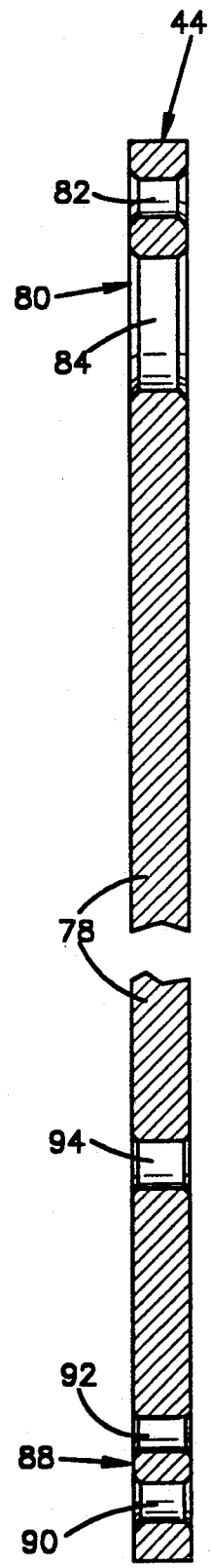
FIG. 6 is a sectional view, taken generally along the line 6—6 of FIG. 5, further illustrating the construction of the flat bender.

A surgically implantable member or spine plate 30 (FIG. 1) is connectable with spinal bodies of a human spinal column to maintain the spinal bodies in a desired relationship. The rigid stainless steel spine plate 30 has a plurality of longitudinally extending slots 32 disposed along the longitudinal central axis of the spine plate. Fasteners are used to interconnect the spine plate and vertebrae in a known manner. The rigid metal spine plate 30 may be mounted in a spinal column in the manner described in U.S. Pat. No. 4,611,581, issued Sep. 16, 1986 and entitled "Apparatus for Straightening Spinal Columns". The fasteners used to connect the spine plate 30 with the spinal column may have the construction disclosed in U.S. Pat. No. 4,854,311, issued Aug. 8, 1989 and entitled "Bone Screw".

A second surgically implantable member or rod 36 is illustrated in FIG. 2. The cylindrical stainless steel rod can be contoured to have a desired configuration in both the sagittal plane and the coronal plane. The spine plate 30 cannot be contoured in the coronal plane. The spinal rod 36 can be connected with various spinal bodies by using fasteners in the manner disclosed in U.S. Pat. No. 4,648,388, issued Mar. 10, 1987 and entitled "Apparatus and Method for Maintaining Vertebrae in a Desired Relationship."

Regardless of whether the spine plate 30 or the cylindrical rod 36 is to be used in the correction of a spinal column, it is believed that it will be frequently be necessary or desirable to contour the implant to correspond to the contour of the spinal column with which it is to be connected. This is particularly true when screws or other fasteners are used to anchor the implant directly to vertebrae or adjacent bones.

Contouring Instruments

A pair of flat benders 42 and 44 (FIGS. 3–6) can be used to contour both the rigid spine plate 30 (FIG. 1) and the rod 36 (FIG. 2). Thus, the flat bender 42 has a rectangular stainless steel body 48 with an upper (as viewed in FIGS. 3 and 4) end portion 50 in which a horizontal metal outer slot 52 and a vertical inner slot 54 are formed. The slots 52 and 54 are engageable with a spine plate 30 to grip the spine plate during contouring of the spine plate.

In addition, the body 48 of the flat bender 42 has a lower end portion 58 (FIGS. 3 and 4) with a plurality of circular holes or openings 60, 62, and 64 which are engageable with a spine rod 36. The hole 60 is larger than the hole 62 and is adapted to engage a larger diameter spine rod than the hole 62. Similarly, the hole 64 is larger than the hole 60 and is adapted to engage and allow pass through of a spine rod that can be accommodated by hole 60 even after a right angle bend has been placed in the rod. A pair of posts 68 and 70 project from opposite sides of the body 48 of the flat bender 42. The stainless steel posts 68 and 70 have enlarged head end portions 74 (FIG. 4) which are adapted to hold a portion of a spine rod 36 in place against the body 48.

The flat bender 44 (FIGS. 5 and 6) has the same general construction as the flat bender 42 of FIG. 3 and 4. However, the flat bender 44 does not have posts corresponding to the posts 68 and 70 of the flat bender 42. Thus, the flat bender 44 has a rectangular stainless steel body 78 with an upper (as viewed in FIGS. 5 and 6) end portion 80 in which slots are formed to engage a spine plate 30. The slots in the upper end portion 80 of the flat bender 44 include an outer or horizontal slot 82 and an inner or vertical slot 84.

The opposite or lower (as viewed in FIGS. 5 and 6) end portion 88 of the flat bender 44 is provided with circular openings or holes to engage a spine rods 36. Thus, the flat bender 44 is provided with circular openings 90, 92, and 94 which are the same size as the openings 60, 62 and 64 in the lower end portion of the flat bender 42.

In one specific preferred embodiment of the flat benders 42 and 44, the benders had an overall length of approximately 17.8 inches (452 mm) and an overall width of approximately 1.25 inches (31.8 mm). The horizontal and vertical slots 52, 54, 82 and 84 for receiving spine plates 30, each had a length of 0.89 inches (22.6 mm) and a width of 0.25 inches (6.4 mm).

The circular holes or openings 60 and 90 for receiving spine rods 36 had a diameter of 0.261 inches (6.63 mm), the openings 62 and 92 had a diameter of 0.219 inches (5.6 mm), and the openings 64 and 94 had a diameter of 0.329 inches (8.33 mm). The posts 68 and 70 of the flat bender 42 had end portions with a diameter of 0.375 inches (9.54 mm) and projected from each side of the flat bender 42 for a distance of 0.48 inches (12.2 mm). To enable adequate leverage to be obtained with the flat benders 42 and 44, the holes 64 and 94 are spaced from the slots 52 and 82 by a distance of approximately 17 inches which is more than ten times the length of any one of the slots 52, 54, 82 and 84.

The foregoing specific dimensions for the flat benders 42 and 44 have been set forth herein for purposes of clarity of description and not for purposes of limiting the invention. Thus, it is contemplated that the flat benders 42 and 44 will be constructed with many different dimensions.

Although a spine rod 36 can be contoured to desired configurations using just the flat benders 42 and 44, it is believed that it may be advantageous to use a tube bender 100 (FIG. 7) in association with either another tube bender or a flat bender when forming some contours in a spine rod. The stainless steel tube bender 100 includes a cylindrical tubular handle 102 from which a cylindrical bending tube 104 extends. A retainer screw 106 is rotatable to grip a spine rod inserted into the tube bender 100. When a spine rod 36 is inserted into the tube bender 100, the spine rod may extend completely through the tube bender or may be so short as to terminate after the retainer screw 106.

Contouring Spine Plates

Figure 8:
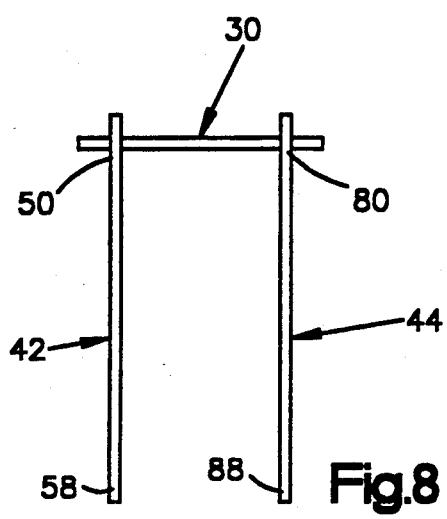
FIG. 8 is a schematic illustration depicting the manner in which the flat benders of FIGS. 3 and 5 are placed in engagement with portions of the spine plate of FIG. 1 prior to bending of the spine plate.
Figure 9:
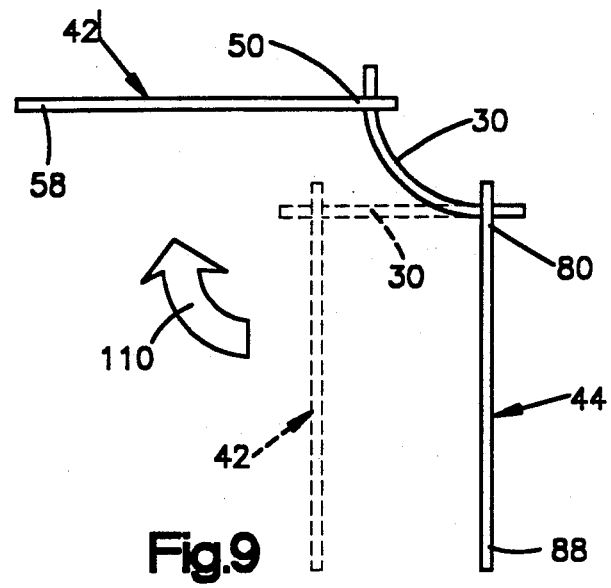
FIG. 9 is a schematic illustration depicting the relationship between the spine plate and flat benders of FIG. 8 after bending of the spine plate with the flat benders.

The spine plate 30 can be bent to have a curve in the sagittal plane by using the flat benders 42 and 44 (FIGS. 3–6) in the manner illustrated schematically in FIGS. 8 and 9. Thus, the straight spine plate 30 is inserted into the horizontal slot 52 (FIGS. 3 and 4) in the flat bender 42 and into the horizontal slot 82 (FIGS. 5 and 6) in the flat bender 44. At this time, the straight longitudinal central axis of the spine plate 30 extends perpendicular to the longitudinal central axes of the flat benders 42 and 44, in the manner shown schematically in FIG. 8.

Once the spine plate has been engaged in the slots 52 and 82 in the upper (as viewed in FIG. 8) end portions 50 and 80 of the flat benders 42 and 44, the flat benders are manually moved apart. This movement plastically deforms the spine plate 30 from its original straight configuration (FIG. 8) to a curved configuration (FIG. 9). The curved configuration is formed so as to more closely correspond to a desired configuration for connection with a spinal column.

To plastically deform the spine plate 30, force is manually applied to the lower end portions 58 and 88 of the flat benders 42 and 44. This force moves the lower end portions 58 and 88 of the flat benders relative to each other to bend the spine plate 30 from the straight configuration shown in FIG. 8 to the curved configuration shown in FIG. 9. Thus, the flat bender 42 is manually pulled away from the flat bender 44, in the manner indicated by the arrow 110 in FIG. 8. As the flat bender 42 is moved along arcuate path away from the flat bender 44, the longitudinal central axes of the flat benders 42 and 44 are maintained in a vertical plane containing the longitudinal central axis of the spine plate 30. Although it is preferred to move the flat bender 42 while the flat bender 44 remains stationary, the flat benders 42 and 44 could both be moved if desired.

The extent of the bend in the spine plate 30 is determined by the surgeon in the operating room. Thus, the surgeon views the spinal column to which the spine plate 30 is to be connected. The surgeon then moves the flat benders 42 and 44 relative to each other to impart the desired curvature to the spine plate 30. Of course, if too much or too little curvature is imparted to the spine plate 30, the flat benders 42 and 44 may be utilized to modify the curvature of the spine plate to more closely correspond to the desired curvature for connection with the spinal column.

Figure 10:
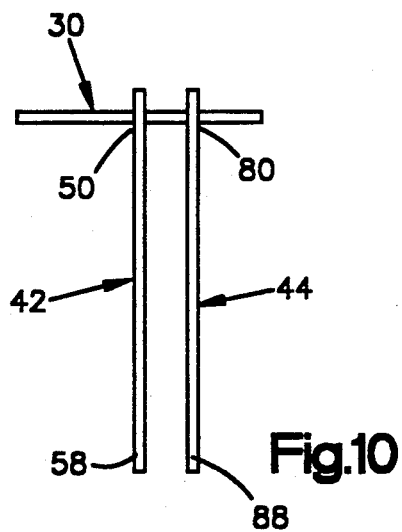
FIG. 10 is a schematic illustration of the manner in which the flat benders of FIGS. 3 and 5 engage the spine plate of FIG. 1 prior to forming a sharp bend in the spine plate.

It is contemplated that it may be desirable to impart a relatively sharp bend to a spine plate 30 rather than the long sweeping bend shown in FIG. 9. When a relatively sharp bend is to be imparted to a spine plate 30, the flat benders 42 and 44 are positioned relatively close together on the spine plate, as shown in FIG. 10. The spine plate 30 extends through the horizontal slots 52 and 82 in the flat benders 42 and 44.

Figure 11:
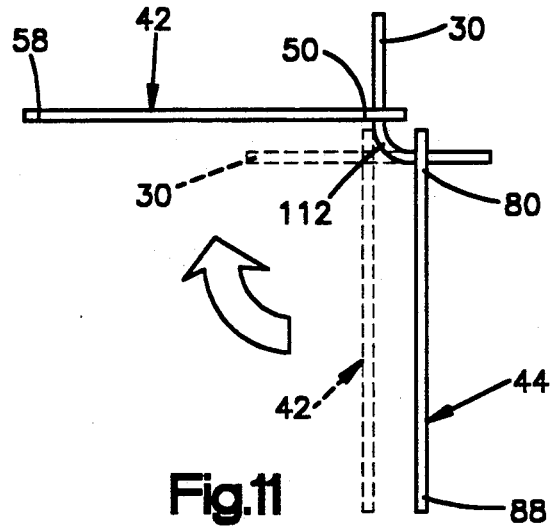
FIG. 11 is a schematic illustration depicting the relationship between the spine plate and flat benders of FIG. 10 after forming a sharp bend in the spine plate with the flat benders.

The spine plate 30 is then plastically deformed by manually applying force to the lower end portions 58 and 88 (FIG. 10) of the flat benders 42 and 44. The force is effective to move the flat benders 42 and 44 relative to each other to form a relatively sharp bend 112 in the spine plate 30. The relatively sharp bend 112 (FIG. 11) in the spine plate 30 has an angle of approximately 90°. Of course, if a lesser angle was desired, the arc through which the flat bender 42 is moved relative to the flat bender 44 would be smaller. Varying the distance which the upper end portions 50 and 80 of the flat benders 42 and 44 are spaced apart along the spine plate 30 enables the sharpness of the bend 112 to be varied.

Figure 12:
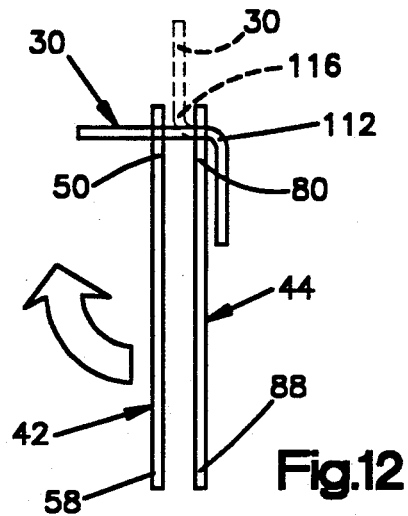
FIG. 12 is a schematic illustration of the manner in which the flat benders of FIGS. 3 and 4 engage the spine plate to form a second sharp bend immediately adjacent to the sharp bend formed in FIGS. 10 and 11.
Figure 13:
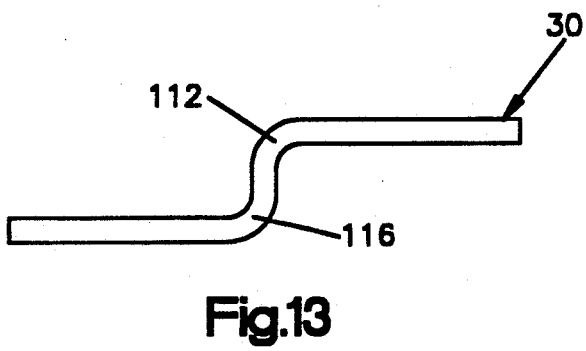
FIG. 13 is a side elevational view of the spine plate of FIG. 1 after a pair of sharp bends have been formed in the spine plate.

It is contemplated that it may be desirable to form a pair of relatively sharp bends in a spine plate 30 in such a manner as to form the spine plate with a step-off, that is, to form the spine plate 30 with the configuration illustrated in FIG. 13. After the sharp bend 112 has been formed in the manner illustrated schematically in FIGS. 10 and 11, the spine plate 30 is withdrawn from the horizontal slots 52 and 82 in the flat benders 42 and 44. The bent spine plate 30 is then rotated through 180° from the orientation shown in FIG. 11. The bent spine plate 30 is then reinserted into the horizontal slots 52 and 82 in the flat benders 42 and 44 in the manner illustrated schematically in FIG. 12.

At this time, both of the flat benders 42 and 44 will be located on the same side of the sharp bend 112. The flat bender 44 will be as close as possible to the sharp bend 112 and the flat bender 42 will be close to the flat bender 44. Force is then manually applied to the lower (as viewed in FIG. 12) end portions 58 and 88 of the flat benders 42 and 44. This force moves the flat bender 42 away from the flat bender 44 to plastically deform the spine plate 30 and form a second sharp bend 116 (FIG. 13) in the spine plate 30. Of course, the angles at the bends 112 and 116 could be any desired angle, other than the illustrated 90°.

For certain spinal columns, it is desirable to impart an axial twist to a spine plate 30. The axial twist enables fasteners which connect the spine plate 30 with the spinal column to exit from the spine plate in different directions.

When an axial twist is to be imparted to a spine plate 30, end portions of the spine plate are inserted into the vertical slots 54 and 84 (FIGS. 3-6) in the flat benders 42 and 44. When this has been done, the flat major side surfaces of the spine plate 30 are disposed in planes which extend parallel to the longitudinal central axes of the flat benders 42 and 44. Force is then manually applied to the lower (as viewed in FIG. 14) end portions 58 and 88 of the flat benders 42 and 44. This force rotates the flat benders 42 and 44 about the longitudinal central axis of the spine plate 30.

The force which is manually applied to the end portions 58 and 88 of the flat benders 42 and 44 moves the flat benders relative to each other in directions extending into and out of the plane of the drawing in FIG. 14. As the flat benders 42 and 44 move, they are rotated about the longitudinal central axis of the spine plate 30. The flat benders 42 and 44 move from positions in which the longitudinal central axes of the flat benders are disposed in a common vertical plane (FIG. 14) to the orientation shown in FIG. 15 in which the longitudinal central axes of the flat benders are offset by 90° from each other.

As the flat benders 42 and 44 are moved relative to each other under the influence of the manual force applied to end portions 58 and 88 of the flat benders, the spine plate 30 is twisted about its longitudinal central axis to the configuration shown in FIG. 16. Of course, varying the extent of relative movement between the flat benders 42 and 44 varies the extent of the twist in the spine plate 30. It is contemplated that, in certain situations, the spine plate 30 will be twisted through an angle which is less than 90°.

Once the spine plate 30 has been bent and/or twisted, the spine plate 30 is connected with a human spinal column. If initial placement of the spine plate on the spinal column indicates that the desired bend and/or twist has not been obtained, the flat benders 42 and 44 can be used to adjust the contour of the spine plate before it is connected with the spinal column. Once the desired contour has been imparted to the spine plate to the flat benders 42 and 44, the spine plate is connected with the spinal column in the manner similar to that described in the aforementioned U.S. Pat. No. 4,611,581.

Spine Rod Contouring

Figure 7:
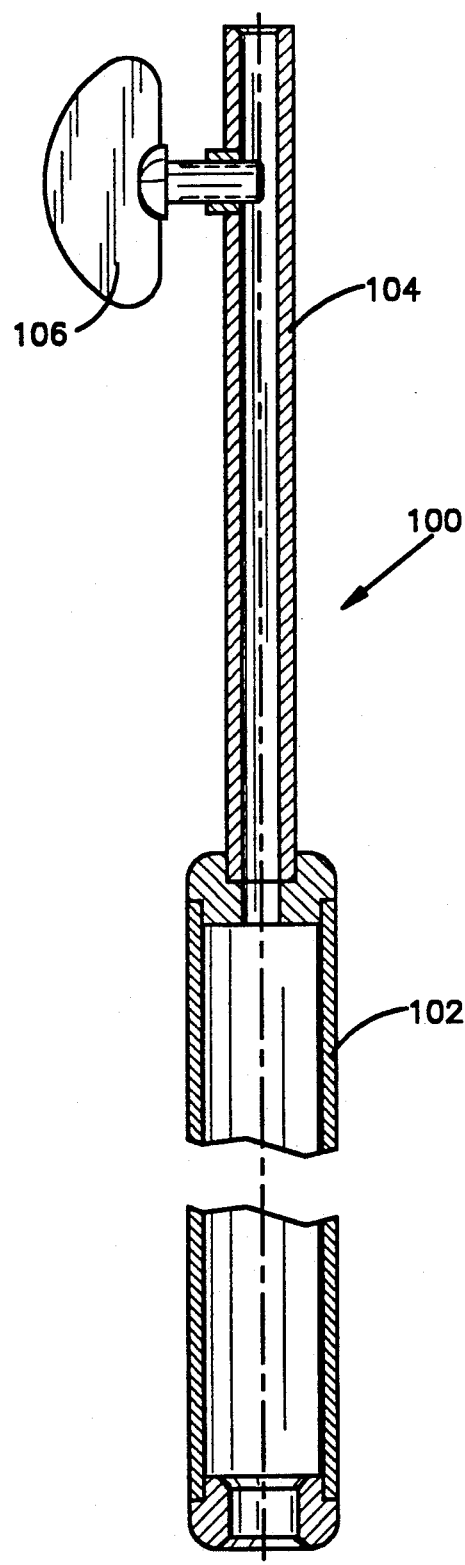
FIG. 7 is a sectional view illustrating the construction of a tube bender.

The spine rod 36 can be contoured in all three planes or a combination of planes to accommodate three dimensional deformities of a spinal column. In order to form a single simple bend in the spine rod 36, a pair of tube benders 100 and 122 (FIG. 17) are connected with the spine rod 36. The tube bender 122 has the same construction as the tube bender 100 (FIG. 7).

When the stainless steel spine rod 36 is to be bent or plastically deformed, the desired location of the bend is marked along the length of the spine rod. The spine rod 36 is then telescopically inserted into the tube bender 100 and the retainer screw 106 tightened. At this time, the desired location of the bend in the spine rod 100 is adjacent to the outer end portion of the bending tube 104. For the specific bend to be formed in the spine rod 36 of FIG. 17, the spine rod extends through the cylindrical passage in the bending tube 104 and into the cylindrical passage in the handle 102 of the tube bender 100.

The tube bender 122 is then telescoped over the opposite end of the spine rod 122 and moved into abutting engagement with the tube bender 100, as shown in FIG. 17. After the retaining screw for the tube bender 122 has been tightened to securely grip the spine rod 36, the spine rod is plastically deformed from the linear configuration shown in FIG. 17 to the contoured or bent configuration shown in FIG. 18. This is accomplished by manually applying force to the tube benders 100 and 122.

The tube benders 100 and 122 are moved relatively to each other from the position shown in FIG. 17 to the position shown in FIG. 18 under the influence of the manually applied force. Thus, in this specific instance, the tube bender 122 is held stationary while the tube bender 100 is moved through an arc of 90° to form a right angle bend in the spine rod 36 (FIG. 18). Once the right angle bend has been formed in the spine rod 36, the tube bender 122 is disengaged from the spine rod 36.

Figure 19:
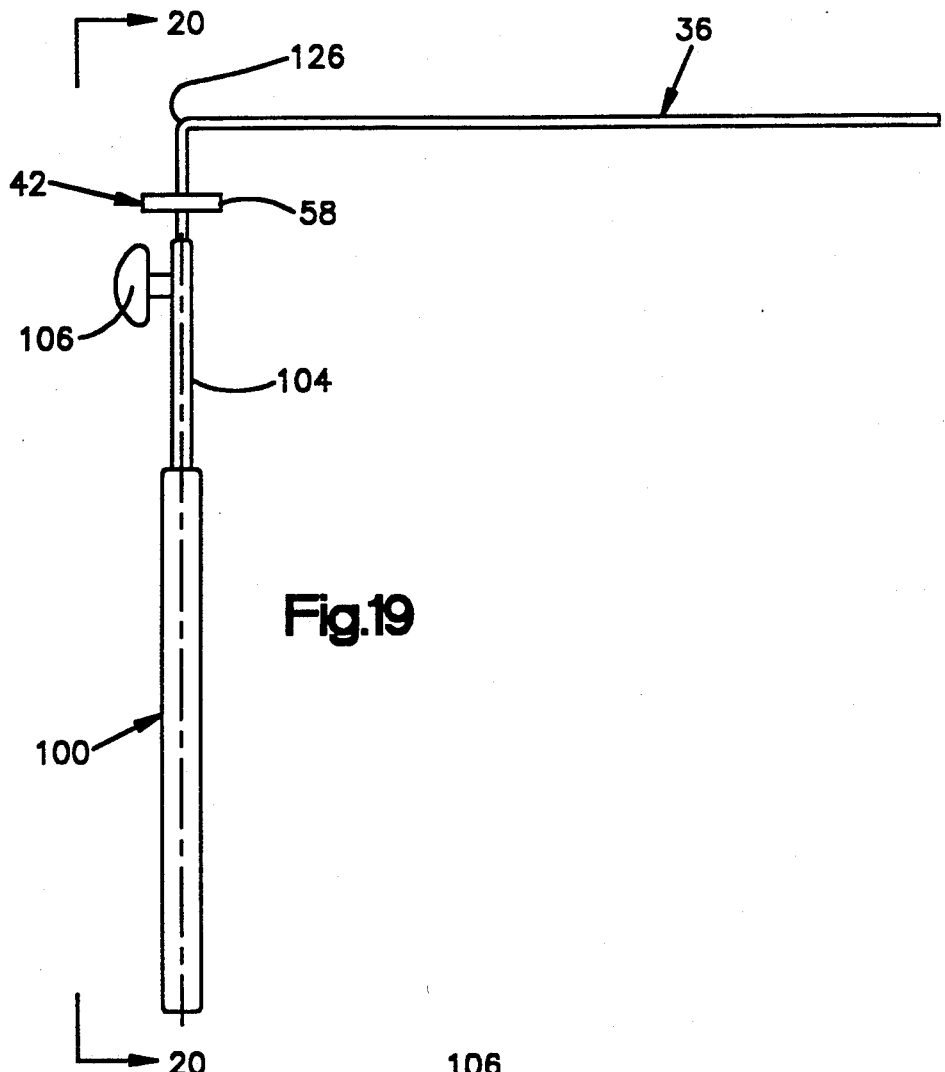
FIG. 19 is an elevational view illustrating the manner in which the bent rod of FIG. 18 is engaged by the tube bender of FIG. 7 and by the flat bender of FIG. 2 prior to the forming of a second bend in the rod.
Figure 20:
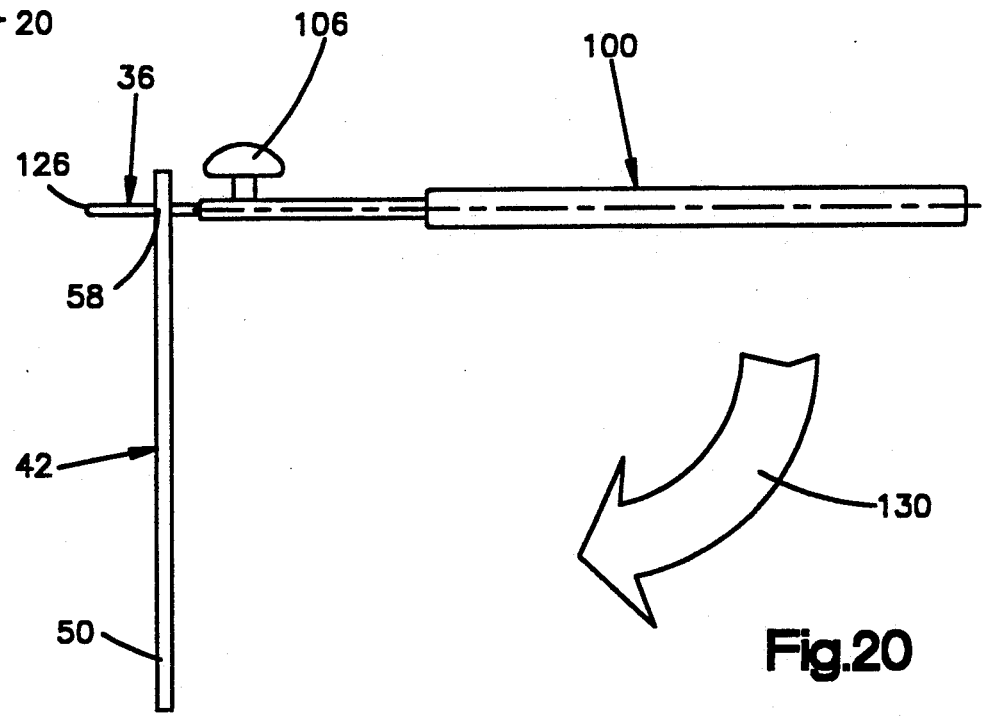
FIG. 20 is a side elevational view further illustrating the relationship between the rod, tube bender, and flat bender of FIG. 20.

In the specific example illustrated in FIGS. 19 and 20, a second bend is to be formed in the spine rod 36. Since the first bend 126 (FIG. 19) has been formed in the spine rod, the two tube benders 100 and 122 cannot be used to form the second bend in the spine rod 36. Therefore, the flat bender 42 is used in association with the tube bender 100 to form the second bend in the spine rod 36.

When the second bend is to be formed in the spine rod 36, the tube bender 100 is first moved along the spine rod to the position where the second bend is to be formed. The retainer screw 106 is then tightened to hold the spine rod 36 against movement relative to the tube bender 100. The spine rod 36 is then inserted through an opening 60 or 62 in the flat bender 42. Thus, the spine rod 36 is inserted through the opening 60 in the end portion 58 of the flat bender 42. The flat bender 42 is then moved along the spine rod, around the first bend 126, to the position shown in FIGS. 19 and 20 adjacent to the tube bender 100.

Force is then manually applied to the flat bender 42 and tube bender 100 to move them relative to each other, in the manner indicated schematically by the arrow 130 in FIG. 20. In this specific instance, the flat bender 42 is held stationary while the tube bender 100 is moved toward the tube bender. This results in the formation of a second bend in the spine rod 36 adjacent to the upper (as viewed in FIG. 20) end of the tube bender 100. Although the bend 126 has been shown as being a 90° bend, the bend 126 and the second bend could be larger or smaller than 90°. Of course, the flat bender 42 can be used to form any desired number of bends of any desired magnitude in the spine rod 36.

Although the tube bender 100 has been used in combination with the flat bender 42 to form the second bend in the spine rod 36, the two flat benders 42 and 44 could have been used. Thus, the spine rod 36 could have been inserted through the opening 60 in the lower end portion 58 of the flat bender 42 (FIG. 3) and through the opening 90 in the lower end portion 88 of the flat bender 44. Force could then be manually applied to the two flat benders 42 and 44 to move the flat benders relative to each other to form a bend in the spine plate 36. Whether a combination of the flat bender 42 and the tube bender 100 or the two flat benders 42 and 44 are used to form a particular bend in the spine rod 36 will depend upon the configuration of the bend or bends to be formed in the spine rod, their location relative to each other, and the preference of the surgeon bending the spine rod.

In the foregoing description, the cylindrical spine rod 36 has been described as being inserted into one of the circular openings 60 or 62 in the flat bender 42 and/or one of the circular openings 90 or 92 in the flat bender 44. However, it is contemplated that it may be preferred to use a horizontal slot 52 or 82 in the flat bender 42 or 44 to form the bends in the spine rod 36 It is believed that the use of the horizontal slot 52 may be particularly advantageous when the flat bender 42 is used in association with the tube bender 100. This is because it is believed that it may be somewhat easier to insert the spine rod 36 into the slot 52 and to move the flat bender 42 relative to the spine rod when the spine rod is inserted in the horizontal slot 52.

Figure 21:
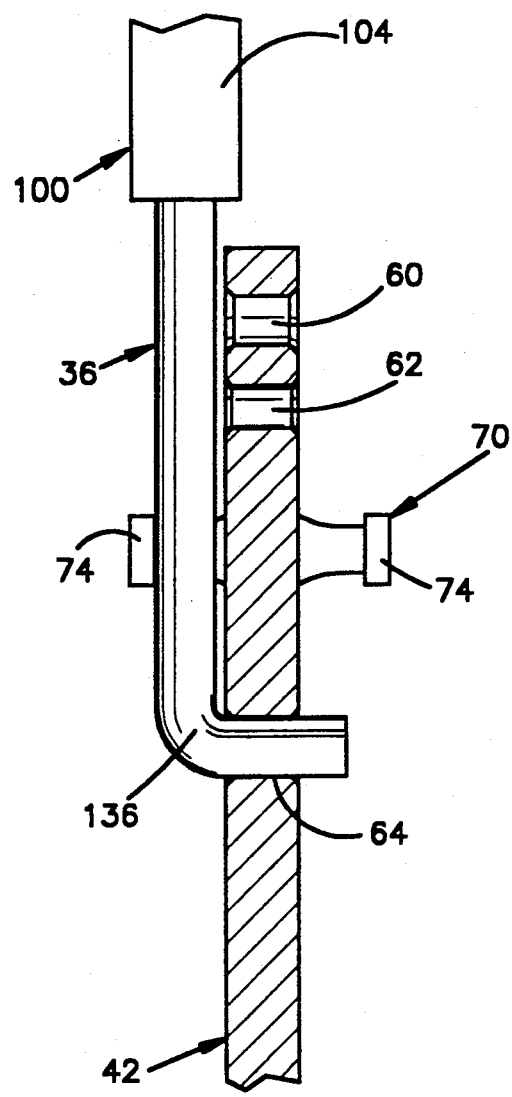
FIG. 21 is an enlarged sagittal plane fragmentary view illustrating the manner in which a portion of a bent rod is engaged by a pair of posts of the flat bender of FIG. 3 and the manner in which the tube bender of FIG. 7 engages a portion of a rod prior to bending of the rod.

When the flat bender 42 and tube bender 100 are being used to plastically deform a spine rod 36 in which one or more bends have already been formed, a portion of the spine rod 36 may be gripped between the posts 68 and 70 (FIG. 3) in the manner illustrated in FIG. 21. Thus, a bend 136 in the spine rod 36 (FIG. 21) is positioned adjacent to the hole 64 of the flat bender 42. A portion of the spine rod 36 (usually the longer portion) extends between the posts 68 and 70 and is held in place by the head end portions 74 of the posts. The spine rod 36 is inserted into the tube bender 100 in the manner previously explained.

During relative movement between the flat bender 42 and the tube bender 100, the posts 68 and 70 cooperate with the spine rod 36 to hold the spine rod against movement relative to the flat bender 42. This allows the tube bender 100 to be moved in relation to flat bender 42, thus changing the sagittal plane position of the rod distal to bend 136 in relation to the position of spine rod 36 beyond bend 126.

Figure 22:
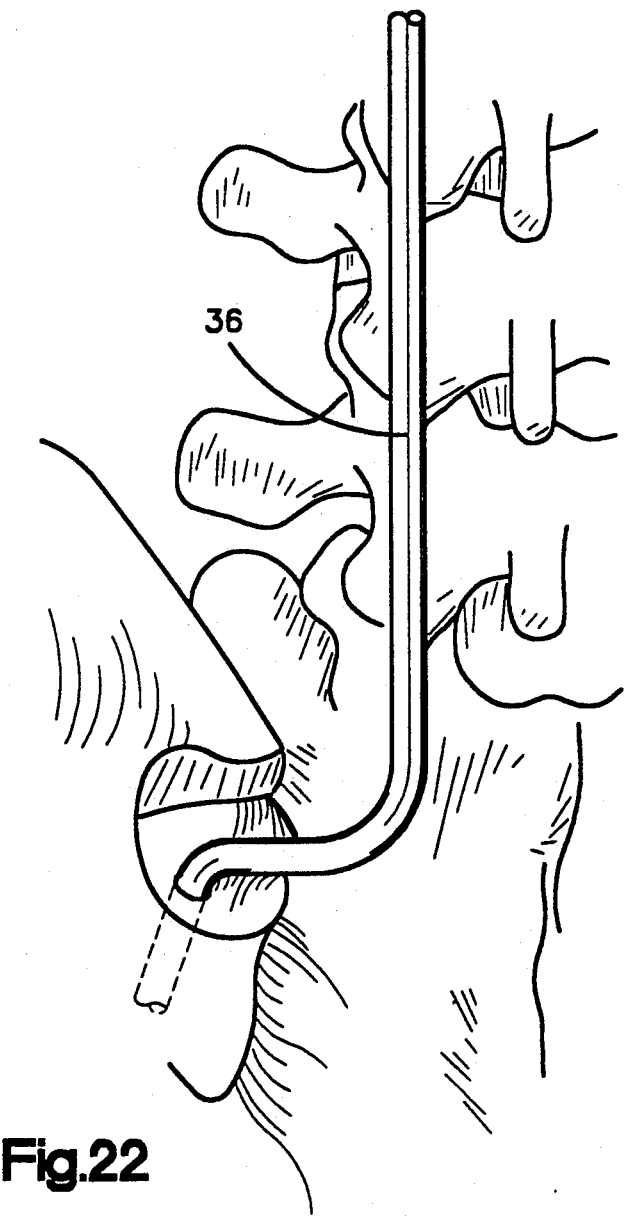
FIG. 22 is an illustration of a contoured rod in place.

Once the spine rod 36 has been contoured to a configuration which corresponds to a desired configuration for connection with a spinal column, the spine rod 36 is loosely positioned on the spinal column in the manner shown in FIG. 22. If, at this time, it is determined that the curvature of the spine rod 36 is not precisely correct, the surgeon can use the flat benders 42 and 44 or the tube benders 100 and 122 or a combination of a flat bender and tube bender to change the configuration of the spine rod to a configuration which provides a better fit with the spinal column to which it is to be connected. The properly contoured spine rod 36 can be connected with the spinal column in the manner described in U.S. Pat. No. 4,648,388. Of course, if desired, other known arrangements could be used for connecting the spine rod 36 with the spinal column.

Conclusion

The present invention provides a new and improved method and apparatus for use in plastically deforming spine plates 30 and/or rods 36 to a desired configuration for connection with a spinal column. The apparatus for plastically deforming the spine plates 30 and/or rods 36 includes a pair of flat benders 42 and 44 which are engageable with either a spine plate or rod and a pair of tube benders 100 which are engageable with a rod. The flat benders 42 and 44 may be used to bend and/or twist a spine plate 30. The flat benders 42 and 44 may also be used either together or with a tube bender 100 to bend a rod 36.

From the above description of the invention, those skilled in the art will perceive improvements, changes and modifications. Such improvements, changes and modifications within the skill of the art are intended to be covered by the appended claims.

Having described specific preferred embodiments of the invention, the following is claimed:

1. An apparatus for use in bending rods and plates to be connected to a spinal column, said apparatus comprising a first longitudinally extending flat bender, said first flat bender having first and second parallel major side surfaces and a first end portion with first surface means for defining a first elongated slot extending through said first flat bender between said first and second major side surfaces to receive a first portion of a plate, said first elongated slot having a longitudinal central axis extending perpendicular to a longitudinal central axis of said first flat bender, said first surface means including a first end surface defining a first end portion of said first elongated slot, a second end surface defining a second end portion of said first elongated slot, and a pair of parallel side surfaces extending between said first and second end portions of said first elongated slot, said first flat bender having a second end portion with second surface means for defining a first circular opening extending through said first flat bender between said first and second major side surfaces to receive a first portion of a rod, said first circular opening having a central axis which intersects and extends perpendicular to a longitudinal central axis of said first flat bender, a second longitudinally extending flat bender, said second flat bender having third and fourth parallel major side surfaces and a first end portion with third surface means for defining a first elongated slot extending through said second flat bender between said third and fourth major side surfaces to receive a second portion of a plate having a first portion received by the first elongated slot in said first flat bender, said second elongated slot having a longitudinal central axis extending perpendicular to a longitudinal central axis of said second flat bender, said third surface means including a first end surface defining a first end portion of said first elongated slot in said second flat bender, a second end surface defining a second end portion of said first elongated slot in said second flat bender, and a pair of parallel side surfaces extending between said first and second end portions of said first elongated slot in said second flat bender, said second flat bender having a second end portion with fourth surface means for defining a first circular opening extending through said second flat bender between said third and fourth major side surfaces to receive a second portion of a rod having a first portion received by an opening in said first flat bender, said first circular opening in said second flat bender having a central axis which intersects and extends perpendicular to a longitudinal central axis of said second flat bender, said first and second flat benders being movable relative to each other under the influence of force manually applied to end portions of said first and second flat benders to plastically deform a plate extending through the first slots in said fist and second flat benders, said first and second flat benders being movable relative to each other under the influence of force manually applied to end portions of said first and second flat benders to plastically deform a rod extending through openings in said first and second flat benders.

2. An apparatus as set forth in claim 1 wherein said first slot in said first flat bender is spaced from said first circular opening in said first flat bender by a distance which is at least ten times the length of said first slot in said first flat bender and said fist slot in said second flat bender is spaced from said first circular opening in said second flat bender by a distance which is at least ten times the length of said first slot in said second flat bender to provide leverage for the force manually applied to end portions of said first and second flat benders during the plastic deformation of a plate and during the plastic deformation of a rod.

3. An apparatus as set forth in claim 1 wherein said first end portion of said first flat bender further includes fifth surface means for defining a second elongated slot extending through said first flat bender between said first and second major side surfaces of said first flat bender to receive a first portion of a plate, said second elongated slot in said first flat bender having a longitudinal central axis extending perpendicular to the longitudinal central axis of said first slot in said first flat bender and parallel to the longitudinal central axis of said first flat bender, said fifth surface means including a first end surface defining a first end portion of said second elongated slot in said first flat bender, a second end surface defining a second end portion of said second elongated slot in said first flat bender, and a pair of parallel side surfaces extending between said first and second end portions of said second elongated slot in said first flat bender, said first end portion of said second flat bender further including sixth surface means for defining a second elongated slot extending through said second flat bender between said first and second major side surfaces of said second flat bender to receive a second portion of a plate having a first portion received by the second elongated slot in said first flat bender, said second elongated slot in said second flat bender having a longitudinal central axis extending perpendicular to the longitudinal central axis of said first slot in said second flat bender and parallel to the longitudinal central axis of said second flat bender, said sixth surface means including a first end surface defining a first end portion of said second elongated slot in said second flat bender, a second end surface defining a second end portion of said second elongated slot in said second flat bender, and a pair of parallel side surfaces extending between said first and second end portions of said second elongated slot in said second flat bender.

* * * * *